United States Patent
Cobb et al.

(10) Patent No.: US 6,984,604 B2
(45) Date of Patent: Jan. 10, 2006

(54) SUPPORTED BIS(PHOSPHORUS) LIGANDS AND THEIR USE IN THE CATALYSIS

(75) Inventors: Michael W. Cobb, Wilmington, DE (US); Weiming Qiu, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 103 days.

(21) Appl. No.: 10/305,230

(22) Filed: Nov. 26, 2002

(65) Prior Publication Data

US 2003/0153691 A1 Aug. 14, 2003

Related U.S. Application Data

(60) Provisional application No. 60/333,365, filed on Nov. 26, 2001.

(51) Int. Cl.
*B01J 31/00* (2006.01)

(52) U.S. Cl. .................. 502/159; 502/164; 502/166; 502/326; 502/402; 502/406; 560/100; 564/180; 549/374

(58) Field of Classification Search ............ 502/159, 502/164, 166, 326, 402, 406; 560/100; 564/180; 564/549/374
See application file for complete search history.

(56) References Cited

U.S. PATENT DOCUMENTS

| | | | |
|---|---|---|---|
| 3,391,115 A | 7/1968 | Kuenstler et al. | |
| 3,496,215 A | 2/1970 | Drinkard et al. | |
| 3,631,191 A | 12/1971 | Kane et al. | |
| 3,655,723 A | 4/1972 | Drinkard, Jr. | |
| 3,766,237 A | 10/1973 | Chia et al. | |
| 5,432,289 A | 7/1995 | Pugin et al. | |
| 5,512,695 A | 4/1996 | Kreutzer et al. | |
| 6,121,184 A * | 9/2000 | Druliner et al. ............ | 502/159 |

FOREIGN PATENT DOCUMENTS

| | | |
|---|---|---|
| DE | 25 03 867 | 8/1975 |
| EP | 0 418 556 | 3/1991 |
| EP | 1 120 160 | 8/2001 |
| WO | WO 93/03839 | 3/1993 |
| WO | WO 95/14659 | 6/1995 |
| WO | WO 98/05692 | 2/1998 |
| WO | WO 99/06146 | 2/1999 |
| WO | WO 99/62855 | 12/1999 |
| WO | WO 01/21627 | 3/2001 |

OTHER PUBLICATIONS

C.A. Tolman, Homogeneous Nickel–Catalyzed Olefin Hydrocyanation, (1985) pp. 3–47, Advances In Catalysis, vol. 33, Wilmington, Delaware.

Jongsma, Tjeer, et al., Polymer–Bound Bulky–Phosphite Modified Rhodium Hydroformylation Catalysts, Macromol. Symp., (1994) pp. 241–256, vol. 80, The Netherlands.

Behringer, et al., Immobilization and chelation of metal complexes with bifunctional phosphine ligands: a solid–state NMR study, Chem. Commun. (1996) pp. 653–654, Garching, Germany.

Cuny, et al., Practical, High–Yield, Regioselective, Rhodium–Catalyzed Hydroformylation of Functionalized a–Olefins, J. Am. Chem. Soc., (1993) pp. 2066–2068, vol. 115, Cambridge, Massachusetts.

Baker, et al., Chelating Diphosphite Complexes of Nickel(0) and Platinum(0): Their Remarkable Stability and Hydrocyanation Activity, J. Chem. Soc., Chem. Commun. (1991) pp. 803–804, Middlesbrough, Cleveland.

Baker, et al., Chiral Aryl Diphosphites: a New Class of Ligands for Hydrocyanation Catalysis, J. Chem. Soc., Chem. Community (1991) pp. 1292–1293, Great Britain.

Moroz, et al., Heterogenized catalyts for olefin hydroformylation containing cobalt and palladium–cobalt complexes anchored on phosphinated SiO2: a 13C solid–state NMR study, Journal of Molecular Catalysis A: Chemical (1996) pp. 217–233, Russia.

Warshawsky, et al., Synthesis and Thermal Regneration of Polymeric Crown Ethers, Poly. Perp. American Chemical Society, Div. Polym. Chem (1980) pp. 114–115, vol. 21, Israel.

* cited by examiner

*Primary Examiner*—Robert D. Harlan

(57) ABSTRACT

Supported bis(phosphorus) ligands are disclosed for use in a variety of catalytic processes, including the isomerization, hydrogenation, hydroformylation, and hydrocyanation of unsaturated organic compounds. Catalysts are formed when the ligands are combined with a catalytically active metal, such as nickel.

4 Claims, No Drawings

SUPPORTED BIS(PHOSPHORUS) LIGANDS AND THEIR USE IN THE CATALYSIS

FIELD OF THE INVENTION

The invention relates to processed for preparing polymer-supported diols and polymer supported bis(phosphorus) ligands that are useful for a variety of catalytic processes. In particular, the ligands are useful in the hydroformylation and isomerization of unsaturated organic compounds.

BACKGROUND OF THE INVENTION

Phosphorus ligands are ubiquitous in catalysis, finding use for a number of commercially important chemical transformations. Phosphorus ligands commonly encountered in catalysis include phosphines (A), and phosphites (B), shown below. In these representations R can be virtually any organic group. Monophosphine and monophosphite ligands are compounds which contain a single phosphorus atom which serves as a donor to a metal. Bisphosphine, bisphosphite, and bis(phosphorus) ligands, in general, contain two phosphorus donor atoms and normally form cyclic chelate structures with transition metals.

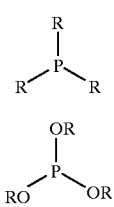

Industrially important catalytic reactions using phosphorus ligands of particular importance are olefin hydrocyanation, hydroformylation and isomerization. Phosphite ligands are particularly good ligands for both of these transformations. For example, the hydrocyanation of ethylenically unsaturated compounds using transition metal complexes with monodentate phosphite ligands is well documented in the prior art. See, for example, U.S. Pat. Nos. 3,496,215, 3,631,191, 3,655,723 and 3,766,237, and Tolman et al., *Advances in Catalysis,* 33, 1, 1985. Bidentate bisphosphite ligands have been shown to be useful in the hydrocyanation of monoolefinic and diolefinic compounds, as well as for the isomerization of non-conjugated 2-alkyl-3-monoalkenenitriles to 3- and/or 4-monoalkene linear nitriles. See, for example, U.S. Pat. Nos. 5,512,695, 5,512, 696 and WO 9514659. Bidentate phosphite ligands have also been shown to be particularly useful ligands in the hydrocyanation of activated ethylenically unsaturated compounds. See, for example, Baker, M. J., and Pringle, P. G., *J. Chem. Soc., Chem. Commun.,* 1292, 1991; Baker et al., *J. Chem. Soc., Chem. Commun.,* 803, 1991; WO 93,03839.

Bidentate phosphite ligands are also useful for alkene hydroformylation reactions. For example, U.S. Pat. No. 5,235,113 describes a hydroformylation process in which an organic bidentate ligand containing two phosphorus atoms linked with an organic dihydroxyl bridging group is used in a homogeneous hydroformylation catalyst system also comprising rhodium. This patent describes a process for preparing aldehydes by hydroformylation of alkenically unsaturated organic compounds, for example 1-octene or dimerized butadiene, using the above catalyst system. Also, phosphite ligands have been disclosed with rhodium in the hydroformylation of functionalized ethylenically unsaturated compounds: Cuny et al., *J. Am. Chem. Soc.,* 1993, 115, 2066. These prior art examples demonstrate the utility of bisphosphite ligands in catalysis.

While these prior art systems represent commercially viable catalysts, they do suffer from significant drawbacks. Primarily, the catalyst, consisting of the ligand and the metal, must be separated from the reaction products. Typically, this is done by removing the product and catalyst mixture from the reaction zone and performing a separation. Typical separation procedures involve extraction with an immiscible solvent, distillation, and phase separations. In all of these examples some of the catalyst, consisting of the ligand and/or the metal, is lost. For instance, distillation of a volatile product from a non-volatile catalyst results in thermal degradation of the catalyst. Similarly, extraction or phase separation results in some loss of catalyst into the product phase. These ligands and metals are often very expensive and thus it is important to keep such losses to a minimum for a commercially viable process.

One method to solve the problem of catalyst and product separation is to attach the catalyst to an insoluble support. Examples of this approach have been previously described, and general references on this subject can be found in "Supported Metal Complexes", D. Reidel Publishing, 1985, *Acta Polymer.* 1996, 47, 1, and Comprehensive Organometallic Chemistry, Pergamon Press, 1982, Chapter 55. Specifically, monophosphine and monophosphite ligands attached to solid supports are described in these references and also in *Macromol. Symp.* 1994, 80, 241. Bisphosphine ligands have also been attached to solid supports and used for catalysis, as described in for example U.S. Pat. No. 5,432,289, *J. Mol. Catal. A* 1996, 112, 217, and *J. Chem. Soc., Chem. Commun.* 1996, 653. The solid support in these prior art examples can be organic, e.g., a polymer resin, or inorganic in nature.

These prior art systems have to date suffered from several drawbacks and have not reached commercial potential. Among the drawbacks noted in the literature are metal leaching and poor reaction rates. In addition, the prior art systems are often not readily amenable to precise control of the ligand coordination properties, e.g., electronics and steric size.

Binaphthol and diol-derived bisphosphite ligands have also been attached to solid supports and used for a number of catalytic processes to give moderate to good results (WO 9906146 and WO 9962855). Lewis acid catalyzed benzylation of phenols is known in the art (see Abdurasuleva, A. R.; Akhmedov, K. N.; Turaeva, M. K., Zh. *Org. Khim.,* 1970, 6, 2108). Alkylation of phenols by olefins is also well-known in the art (see March, *J. Advanced Organic Chem,* 4th Ed., p 536, 1992 and the references therein). It is known that isopropyl aromatics can be converted to 1-methylethenyl aromatics by 2,3-dichloro-5,6-dicyano-1,4-benzoquinone (DDQ) treatment, (see Shishido, K.; Yamashita, A.; Hirova, K.; Fukumoto, K., *J. Chem. Soc., Trans. Perkin I,* 1990, 469). Warshasky et al disclosed alkylating catechol with a chloromethylated styrene-divinylbenzene copolymer (see Warshasky, A.; Kahama, N. *Polym. Prep., Am. Chem. Soc., Div. Polym. Chem.* 1980, 21, 114). Alkylation of phenol with low molecular weight polybutadiene is also disclosed (see JP 11335439 and DE 2503867).

The present invention offers advantages that would be helpful in overcoming the drawbacks of the prior art. Disclosed herein are processes for the reaction of either benzyl halide-containing polymer or olefin-containing polymers with diols to form ligand compositions. All of the ligand compositions of the present invention have carbon-carbon bond linkage between the polymer support and diol (backbone) moiety. The carbon-carbon linkage, unlike functional group linkage, improves the stability of the ligand composition and the catalysts prepared therefrom.

The ligand compositions of the present invention are used to prepare catalysts that are useful for catalytic processes. For example, the catalysts of the present invention are useful for isomerization, hydrogenation, hydrocyanation, and hydroformylation. When removing the catalyst from the product phase of these processes, there is commercial need to avoid loss. The present catalysts are stable, and therefore are more easily separated from the product phase by distillation or extraction than are catalysts having functional group linkages.

SUMMARY OF THE INVENTION

One embodiment of this invention is a process for preparing a polymer-supported diol of the formula:

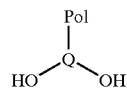

(1)

wherein Pol and Q are connected via a carbon-carbon bond;

Q is an organic ring structure; and

Pol is an insoluble polymer support, said process, comprising: acid-catalyzed grafting a diol onto a polymer selected from the group consisting of a benzyl halide-containing polymer or a olefin-containing polymer wherein said diol is selected from the group consisting of biphenol, C,

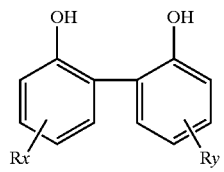

C wherein each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether, wherein neighboring $R^1$ groups are optionally connected to form a ring structure and wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl; and wherein x and y each independently are 0–3 and x and y each independently are 0–4 if at least one of $R_x$ or $R_y$ contains an aromatic ring, and binaphthol, D,

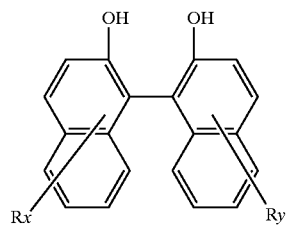

D wherein each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether; wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl, and wherein x and y each independently are 0–5 and x and y each independently are 0–6 if at least one of $R_x$ or $R_y$ contains an aromatic ring, and combinations thereof.

Another embodiment of this invention is a polymer-supported diol as prepared and disclosed herein.

A further embodiment of this invention is a process for preparing a polymer-supported bis(phosphorous) ligand (2) having the formula,

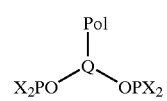

(2)

wherein:
Pol and Q are connected via a carbon-carbon bond;
Q is an organic ring structure; and
Pol is an insoluble polymer support;
X is selected from the group of alkoxide, aryloxide, alkyl or aryl;
said process comprising: contacting a polymer supported diol as disclosed herein with a phosphorous halide of the type PYnX3–n, where
Y is a halide,
X is selected from the group consisting of alkoxide, aryloxide, alkyl and aryl, and n=3, 2, or 1, wherein when X is an alkoxide, aryloxide, alkyl or aryl, X may contain from 1 to 50 carbon atoms, heteroatoms, or functional groups selected from the group consisting of ethers, alcohols, esters, and amides.

Yet another embodiment of this invention is a polymer-supported bis(phosphorous) ligand as prepared and disclosed herein.

Yet another embodiment of this invention is a process for preparing a polymer-supported transition metal catalyst composition of the formula

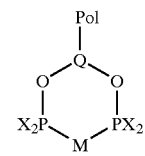

(3)

wherein
Pol and Q are connected via a carbon-carbon bond;
Q is an organic ring structure; and
Pol is an insoluble polymer support;

X is selected from the group of alkoxide, aryloxide, alkyl or aryl;

M is a catalytically active transition metal; said process comprising: combining a polymer-supported bis (phosphorous) ligand as prepared and disclosed herein with a catalytically active transition metal, M.

Yet another embodiment of this invention is a catalyst composition as disclosed and prepared herein.

Yet another embodiment of this invention is an isomerization, hydrogenation, hydrocyanation or hydroformylation process using a catalyst composition as disclosed and prepared herein.

Yet another embodiment of this invention is an isomerization process comprising reacting an unsaturated organic nitrile compound in the presence of the catalyst composition of formula (3) and at least one Group VIII metal wherein the unsaturated organic nitrile contains less than 500 ppm of peroxides.

This process may be run in either the liquid or vapor phase. The polymer-supported catalysts provide significantly improved selectivities and yields in these processes.

Description and Preparation of Supported Biphenols and Binaphthols

Disclosed herein first is a process for preparing support diol compositions followed by a second process for preparing polymer supported bis(phosphorous) ligands via electrophilic substitution reactions. The aims of the second process are achieved by construction of a chelating ligand covalently bonded to an insoluble polymer, which is preferably a polymer support. By "Pol" as used hereinafter we mean, at all times, "insoluble polymer" or "polymer support".

The ligand is grafted onto the Pol via a carbon-carbon linkage. The catalysts of the present invention that are made from these supported compositions are advantageous over similar catalysts having functional groups. These catalysts have a higher activity than catalysts having functional group linkages. The catalyst compositions disclosed herein are useful in isomerization, hydrocyanation, hydrogenation and hydroformylation processes.

The first step is the preparation of a diol group covalently attached to an insoluble polymer or a polymer support, as exemplified by the following structure:

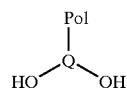
(1)

wherein, Pol, as used hereinafter in the structures represents an insoluble polymer or a polymer support. As used herein, Q means any biphenol or binaphthol that binds the diol moiety to the polymer by carbon-carbon linkage.

a) Grafting Biphenols onto Benzyl Halide-Containing Polymers

The preparation of materials of Formula 1 involves Lewis acid catalyzed grafting biphenols (C) onto benzyl halide-containing polymers. It is preferred to graft biphenols onto benzyl chloride-containing polymers, such as Merrifield resin [copolymer of styrene and vinylbenzyl chloride crosslinked by 0.2% to 5% of divinylbenzene], poly(vinylbenzyl chloride), and copolymer of styrene and vinylbenzyl chloride modified cellulose.

The reaction is catalyzed by a variety of Lewis acids, such as $AlBr_3$, $AlCl_3$, $AlF_3$, $AlCl_xF_{(3-x)}$, $GaCl_3$, $FeCl_3$, $SbCl_5$, $ZrCl_4$, $SnCl_4$, $BCl_3$, $BF_3$, $SbCl_3$, $BF_3 \cdot OEt_2$, $BPh_3$, $ZnCl_2$, alkoxide or phenolate of Al(III), Ga(III), Fe(III), Sb(III), Zr(IV), Sn(IV), and B(III), and other salt forms of these metals, such as triflates or tosylates. "Ph" is used herein to represent the term "phenyl". Preferably, the Lewis acid is $ZnCl_2$ or $AlCl_3$. The grafting temperature is from about 10° C. to about 150° C., preferably about 25° C. to about 100°C.

Solvents that are useful are those that are inert to the grafting reaction and that are able to swell the polymer. These include, but are not limited to, methylene chloride, 1,2-dichloroethane, chlorobenzene, dichlorobenzenes, nitromethane, and dinitrobenzene. The unreacted benzyl chloride group may interfere with the application of the grafted polymer. Optionally, the unreacted benzyl chloride groups could be removed by treatment of the grafted polymer with $AlCl_3$ in toluene during reflux. Unreacted biphenol may be removed and recovered by washing the polymer with a solvent that is suitable as grafting medium, such as methylene chloride and dichloroethane.

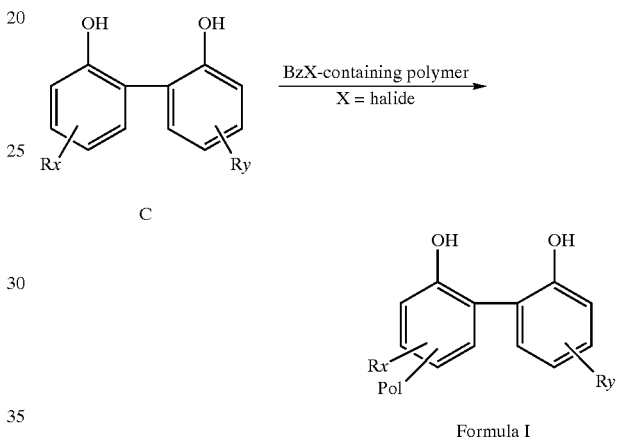

Formula I

Each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether, wherein neighboring $R^1$ groups could be connected to form a ring structure and wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl; and wherein x and y each independently are 0–3 and x and y each independently are 0–4 if at least one of $R_x$ or $R_y$ contains an aromatic ring. Bz is used herein to represent the term "benzyl halide".

b) Grafting Binaphthols onto Benzyl Chloride-Containing Polymers

The preparation of materials of Formula II involves in Lewis acid catalyzed grafting biphenols (D) onto benzyl chloride-containing polymers, such as Merrifield resin [copolymer of styrene and vinylbenzyl chloride crosslinked by 0.2% to 5% of divinylbenzene], poly(vinylbenzyl chloride), and copolymer of styrene and vinylbenzyl chloride modified celluloses.

The reaction is catalyzed by a variety of Lewis acids, such as $AlBr_3$, $AlCl_3$, $AlF_3$, $AlCl_xF_{(3-x)}$, $GaCl_3$, $FeCl_3$, $SbCl_5$, $ZrCl_4$, $SnCl_4$, $BCl_3$, $BF_3$, $SbCl_3$, $BF_3 \cdot OEt_2$, $BPh_3$, $ZnCl_2$, $ZnBr_2$, $ZnI_2$, alkoxide or phenolate of Al(III), Ga(III), Fe(III), Sb(III), Zr(IV), Sn(IV), and B(III), and other salt forms of these metals, such as triflates or tosylates. Preferably, the Lewis acid is $ZnCl_2$ or $AlCl_3$. By "Et" we mean ethyl.

The grafting temperature is from about 10° C. to about 150° C., preferably, about 25° C. to about 100° C. Solvents, which are inert to the grafting reaction and able to swell the polymer, are used for the grafting. These include, but are not limited to, methylene chloride, 1,2-dichloroethane, chlorobenzene, dichlorobenzenes, nitromethane, and dinitrobenzene. The unreacted benzyl chloride group may interfere with the application of the grafted polymer. Optionally, the unreacted benzyl chloride groups could be removed by the treatment with $AlCl_3$ in toluene at reflux. Unreacted binaphthol may be removed and recovered by washing the polymer with proper solvents, such as methylene chloride or dichloroethane or solvents suitable as the grafting medium.

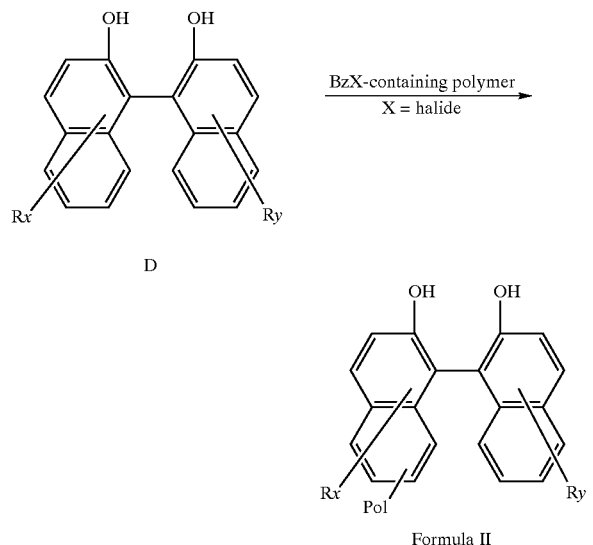

D

Formula II

Each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether; wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl, and wherein x and y each independently are 0–5 and x and y each independently are 0–6 if at least one of $R_x$ or $R_y$ contains an aromatic ring, and combinations thereof. Preferably, each $R^1$ is independently selected from the group consisting of $C_1$ to $C_{20}$ branched or straight chain alkyl, and $C_1$ to $C_{20}$ cycloalkyl; y is 0–5 and y is 0–6 if at least one of $R_x$ or $R_y$ contains aromatic ring(s).

c) Grafting Biphenols onto Olefin-Containing Polymers

The preparation of materials of Formula III involves in acid catalyzed grafting biphenols (C) onto olefin-containing polymers, such as, polybutadiene, copolymer of butadiene and styrene, dehydrogenated polystyrene. The last is prepared by partial dehydrogenation of polystyrene to partially unsaturated backbone structure by the treatment of 2,3-dichloro-5,6-dicyano-1,4-benzoquinone (DDQ).

The grafting reaction is catalyzed by a variety of Lewis acids and protic acids, such as $AlBr_3$, $AlCl_3$, $AlF_3$, $AlCl_xF_{(3-x)}$, $GaCl_3$, $FeCl_3$, $SbCl_5$, $ZrCl_4$, $SnCl_4$, $BCl_3$, $BF_3$, $SbCl_3$, $BF_3.OEt_2$, alkoxide or phenolate of Al(III), and Ga(III), other salt forms of these metals, such as triflates or tosylates, and sulfuric acid, phosphoric acid, polyphosphoric acid, triflic acid, phosphotungstic acid. Preferably, the acid is $AlCl_3$, phosphotungstic acid or triflic acid. The grafting temperature is from about 25° C. to about 180° C., preferably, about 40° C. to about 140° C.

Solvents, which are inert to the grafting reaction and able to swell the polymer, are used for the grafting. These include, but are not limited to, methylene chloride, 1,2-dichloroethane, chlorobenzene, dichlorobenzenes, nitromethane, and dinitrobenzene. When the solvent having a boiling point lower than the reaction temperature is used, the reaction is carried out in an autoclave.

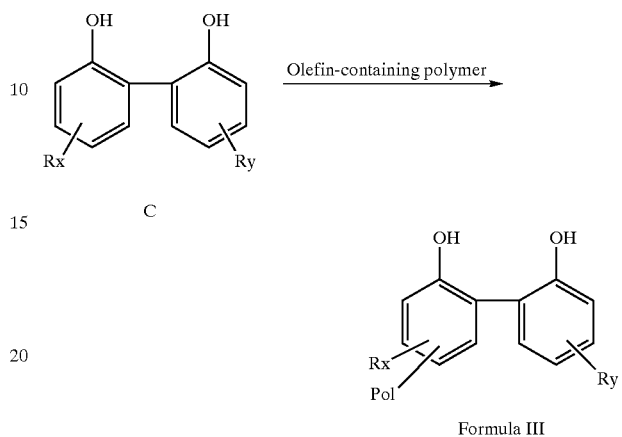

Formula III

Each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether, wherein neighboring $R^1$ groups could be connected to form a ring structure and wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl; and wherein x and y each independently are 0–3 and x and y each independently are 0–4 if at least one of $R_x$ or $R_y$ contains an aromatic ring.

d) Grafting Binaphthols onto Olefin-Containing Polymers

The preparation of materials of Formula IV involves in acid catalyzed grafting binaphthols (D) onto olefin-containing polymers, such as, polybutadiene, copolymer of butadiene and styrene, dehydrogenated polystyrene. The last is prepared by partial dehydrogenation of polystyrene to partially unsaturated backbone structure by the treatment of DDQ.

The grafting reaction is catalyzed by a variety of Lewis acids and protic acids, such as $AlBr_3$, $AlCl_3$, $AlF_3$, $AlCl_xF_{(3-x)}$, $GaCl_3$, $FeCl_3$, $SbCl_5$, $ZrCl_4$, $SnCl_4$, $BCl_3$, $BF_3$, $SbCl_3$, $BF_3.OEt_2$, $BPh_3$, alkoxide or phenolate of Al(III), and Ga(III), other salt forms of these metals, such as triflates or tosylates, and sulfuric acid, phosphoric acid, polyphosphoric acid, triflic acid, phosphotungstic acid. Preferably, the acid is $AlCl_3$, phosphotungstic acid or triflic acid. The grafting temperature is from 25° C. to 180° C., preferably, 40° C. to 140° C.

Solvents, which are inert to the grafting reaction and able to swell the polymer, are used for the grafting. These include, but are not limited to methylene chloride, 1,2-dichloroethane, chlorobenzene, dichlorobenzenes, nitromethane, and dinitrobenzene. When the solvent with its boiling point lower than the reaction temperature is used, the reaction is carried out in an autoclave.

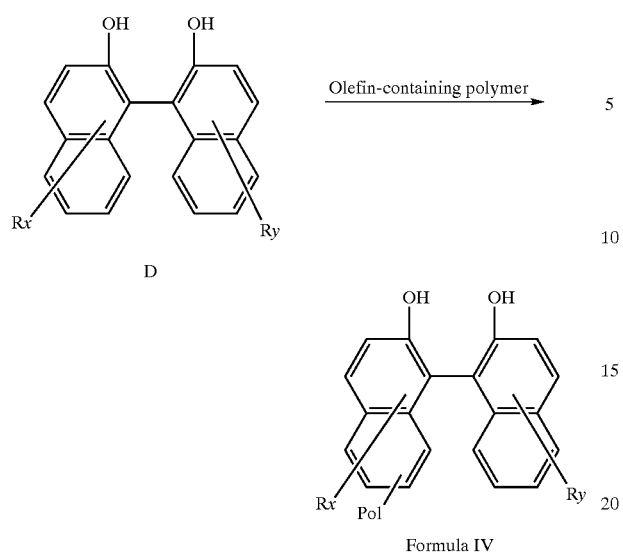

Formula IV

Each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether; wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl, and wherein x and y each independently are 0–5 and x and y each independently are 0–6 if at least one of $R_x$ or $R_y$ contains an aromatic ring, and combinations thereof. Preferably, each $R^1$ is independently selected from the group consisting of $C_1$ to $C_{20}$ branched or straight chain alkyl, and $C_1$ to $C_{20}$ cycloalkyl; y is 0–5 and y is 0–6 if at least one of $R_x$ or $R_y$ contains aromatic ring(s).

The processes described above produce a polymer-supported diol of the formula:

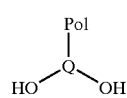 (1)

wherein Pol and Q are connected via a carbon-carbon bond; Q is an organic ring structure; and Pol is an insoluble polymer support; wherein a diol is grafted onto a polymer selected from the group consisting of a benzyl halide-containing polymer or a olefin-containing polymer; and wherein the diols are as described above.

Description and Preparation of Polymer-Supported Bis(Phosphorus) Ligands

Polymer-supported bis(phosphorus) ligands have been prepared by a variety of methods known in the art, for example, see descriptions in WO 93,03839; U.S. Pat. Nos. 4,769,498 and 4,668,651. In general, the transformation involves the reaction of a phosphorus halide, typically but not limited to chloride, with the diol to form P—O bonds. The phosphorus halide may be any compound of the type $PY_nX_{3-n}$, where Y=halide, X=alkoxide, aryloxide, alkyl, aryl, and n=3, 2, or 1. The preferred phosphorus halides of the present invention are those where Y=Cl; X=alkoxide, aryloxide, alkyl, or aryl; and n=1. The group X may contain from 1 to 50 carbon atoms. It may also optionally contain heteroatoms such as oxygen, nitrogen, halogen, and the like, and also functional groups such as ethers, alcohols, esters, amides, as well as others. The groups X may or may not be linked to form a cyclic structure. The $PX_2$ moiety may form a ring and X may also be alkoxide, aryloxide, alkyl, aryl, or a combination of them. Many dialkyl chlorophosphines and diaryl chlorophosphines are commercially available, or may be prepared by methods known in the art, for example, J. Am. Chem. Soc. 1994, 116, 9869. Phosphorochloridites, may be prepared by a variety of methods known in the art, for example, see descriptions in Polymer 1992, 33, 161; Inorg. Syn. 1966, 8, 68; U.S. Pat. No. 5,210,260; Z. Anorg. Allg. Chem. 1986, 535, 221. For example, the reaction of 2,2'-biphenol with phosphorus trichloride gives 1,1'-biphenyl-2,2'-diylphosphorochloridite.

The reaction of these chlorophosphorus reagents with a material of Formula 1 in the presence of a base gives a polymer-supported bis(phosphorus) ligand exemplified by the structure shown:

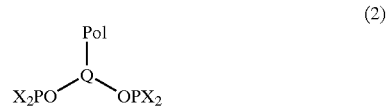 (2)

where X and Q are the same as defined above.

The present invention for preparing the polymer supported bis(phosphorous) ligand of Formula 2 is accomplished by performing additional steps to the process for preparing the polymer supported diol. The composition represented by Formula 1 is reacted with chlorophosphorus reagents in the presence of a base to give a polymer-supported bis(phosphorus) ligand. Bases that are useful in the preparation of these bis(phosphorous) ligands are tertiary amines.

The process for preparing the supported diol compositions as disclosed hereinabove, followed by the process for preparing the ligand compositions of the present invention result in compositions that have electron-donating groups. The presence of these species in the ligands, and ultimately the polymer-supported transition metal catalyst compositions that are made therefrom, are useful, inter alia, in isomerization processes. We further disclose herein a process for the preparation of the polymer-supported transition metal catalyst compositions.

The process described above produces a polymer-supported bis(phosphorous) ligand (2) having the formula,

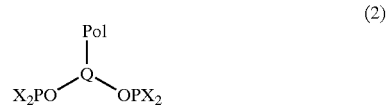 (2)

wherein Pol and Q are connected via a carbon-carbon bond; Q is an organic ring structure; Pol is an insoluble polymer support; and X is selected from the group of alkoxide, aryloxide, alkyl or aryl; which is the reaction product of the polymer supported diol described above with a phosphorous halide of the formula $PY_nX_{3-n}$, wherein Y is a halide; X is selected from the group consisting of alkoxide, aryloxide, alkyl and aryl; and n=3, 2, or 1; and wherein, when X is an alkoxide, aryloxide, alkyl or aryl, X may contain from 1 to 50 carbon atoms, heteroatoms, or functional groups selected from the group consisting of ethers, alcohols, esters, and amides.

Description and Preparation of Polymer-Supported Transition Metal Catalysts

The transition metal catalysts which are a subject of this invention are defined by the formula shown below:

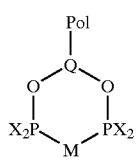
(3)

wherein Q and X are the same as defined above. M is a transition metal capable of carrying out catalytic transformations. M may additionally contain labile ligands which are either displaced during the catalytic reaction, or take an active part in the catalytic transformation. Any of the transition metals may be considered in this regard. The preferred metals are those comprising groups VIII, IX and X of the Periodic Table. The catalytic transformations possible with these catalysts comprise, but are not limited to, isomerization, hydrogenation, hydroformylation and hydrocyanation. The most preferred metal for hydrocyanation and isomerization is nickel, and the preferred metals for hydrogenation, and hydroformylation are rhodium, cobalt, iridium, palladium and platinum, the most preferred being rhodium.

The zero-valent nickel compounds useful in the present invention can be prepared or generated according to techniques well known in the art, as described, for example, U.S. Pat. Nos. 3,496,217; 3,631,191; 3,846,461; 3,847,959; and 3,903,120. Zero-valent nickel compounds that contain ligands which can be displaced by the organophosporus ligands are a preferred source of zero-valent nickel. Such preferred zero-valent nickel compounds are Ni(COD)$_2$ (COD is 1,5-cyclooctadiene), Ni{P(O-o-C$_6$H$_4$CH$_3$)$_3$}$_2$ (C$_2$H$_4$), and Ni(P(O-oC$_6$H$_4$CH$_3$)$_3$)$_3$. These nickel compounds are known in the art. Alternatively, divalent nickel compounds may be combined with a reducing agent, to serve as a source of zero-valent nickel in the reaction. Suitable divalent nickel compounds include compounds of the formula NiY$_2$ where Y is halide, carboxylate, or acetylacetonate. Suitable reducing agents include metal borohydrides, metal aluminum hydrides, metal alkyls, Li, Na, K, or H$_2$.

The process described above produces a polymer-supported catalyst composition of the formula

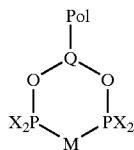
(3)

wherein Pol and Q are connected via a carbon-carbon bond; Q is an organic ring structure; Pol is an insoluble polymer support; X is selected from the group of alkoxide, aryloxide, alkyl or aryl; and M is a catalytically active transition metal; which is a combination of a polymer-supported bis (phosphorous) ligand as described above with a catalytically active transition metal, M.

Isomerization Using Chelating Phosphorus-Containing Ligands:

Improved isomerization processes can be achieved by using reagents with minimum amount of specific harmful impurities. The chelating ligand compositions of the present invention can be used to form catalysts, which may be used for the isomerization of branched nitriles to linear nitriles.

The isomerization comprises contacting an alkenyl nitrile with a catalyst disclosed above under conditions sufficient to isomerize the alkenyl nitrile. The process can be run with or without a Lewis acid. Examples of suitable alkenyl nitrites include, but are not limited to, 2-alkyl-3-monoalkenenitriles, 3-alkenenitriles, or combinations thereof. The isomerization can be carried out under conditions which depend to a certain extent on the particular catalyst being used, the alkenyl nitrile, the volatility of the reagents and products, and the desired rate. An improved process is to use branched nitrites containing less than 500 ppm of peroxides. Preferably, the branched nitrites contain less than 100 ppm of peroxides. Generally, temperatures of about −25° C. to about 200° C. can be used, with 0° C. to about 175° C. being preferred.

A 2-alkyl-3-monoalkenenitrile can be obtained other available sources. The olefinic double bond in the 2-alkyl-3-monoalkenenitriles used as starting materials in the isomerization cannot be conjugated to the triple bond of the cyano group. Suitable starting 2-alkyl-3-monoalkenenitriles can also carry groups that do not attack the catalyst, for example, another cyano group. Preferably, the starting 2-alkyl-3-monoalkenenitriles contain from 5 to 8 carbon atoms, excluding any additional substitution. 2-Methyl-3-butenenitrile is an especially important starting material, because it is isomerized to produce 3-pentene nitrile, which in turn is used to produce adiponitrile. Other representative nitrile starting materials include 2-ethyl-3-butenenitrile and 2-propyl-3-butenenitrile.

When the starting nitrile is 2-methyl-3-butenenitrile, the isomerization products are 3-pentenenitrile and 4-pentenenitrile.

The isomerization process of this invention can be carried out, for example, at atmospheric pressure and at any temperature in the range of 10–200° C., preferably in the range of 60–150° C. The pressure is not critical, however, and can be above or below atmospheric pressure, if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material, and is usually of glass or an inert metal or alloy, such as nickel, copper, silver, gold, platinum, stainless steel, Monel® or Hastelloy®.

The process can be carried out in the absence or in the presence of a solvent or diluent. Any solvent or diluent that is inert to, or nondestructive of, the catalyst can be used. Suitable solvents include, but are not limited to, aliphatic or aromatic hydrocarbons (hexane, cyclohexane, benzene), ethers (diethyl ether, tetrahydrofuran, dioxane, glycol dimethyl ether, anisole), esters (ethyl acetate, methyl benzoate, nitriles (acetonitrile, benzonitrile), or combinations of two or more thereof.

A non-oxidizing environment is desirable in order to retard oxidative deactivation of the catalyst. Accordingly, an inert atmosphere, e.g., nitrogen, is preferably used, although air can be used.

The catalyst (complex of Group VIII metal, preferably nickel, and chelating ligand) is essentially nonvolatile, whereas the 2-methyl-3-butenenitrile reactant and the linear pentenenitrile products are relatively volatile. Accordingly, in a continuous flow procedure, the catalyst can be a component of the flowing system in a liquid or slurry-liquid-phase operation. It can also be in a mobile non-flowing liquid state in a semi-vapor phase operation, or it may be in a fixed-bed state in a conventional flowing vapor-phase operation or flowing liquid-phase operation.

The time required for the isomerization process to obtain a practical level of conversion of, for example, 2-alkyl-3-monoalkenenitrile, to linear alkenenitrile is dependent upon the temperature of reaction, i.e., operation at lower temperature generally requires a longer time than operation at a higher temperature. A practical reaction time can be in the range of a few seconds to many hours (e.g., 2 seconds to about 24 hours), depending on the particular conditions and method of operation.

The molar ratio of 2-alkyl-3-monoalkenenitrile to catalyst is generally greater than 1:1, usually in the range from about 5:1 to 20,000:1, preferably 100:1 to 5,000:1, for a batch or continuous operation.

Hydroformylation Using Chelating Phosphorus-Containing Ligands:

The polymeric ligands of the present invention may be used to form catalysts which may be used for hydroformylation of internal monoethenically unsaturated organic compounds with 2 to 20 carbon atoms or cyclic monoethenically unsaturated compounds with 5 to 20 carbon atoms to produce corresponding aldehydes. The catalyst comprises a Group VIII metal or Group VIII metal compound combined with at least one polymeric ligand of the present invention. Preferred Group VIII metals for hydroformylation reactions are rhodium, iridium, and platinum, the most preferred being rhodium. The Group VIII metal may be in the form of a compound, such as a hydride, halide, organic acid salt, ketonate, inorganic acid salt, oxide, carbonyl compound, amine compound, or combinations of two or more thereof. Preferred Group VIII metal compounds are $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, $[RhCl(COD)]_2$, and combinations of two or more thereof ("acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. Rhodium compounds suitable for hydroformylation can be prepared or generated according to techniques well known in the art, as described, for example, in PCT Patent Application WO 9530680, U.S. Pat. No. 3,907,847, and *J. Am. Chem. Soc.* 1993, 115, 2066, incorporated herein by reference. Rhodium compounds that contain ligands which can be displaced by the present polymeric phosphite ligands, are a preferred source of rhodium. Examples of such preferred rhodium compounds are $Rh(CO)_2$ (acac), $Rh(CO)_2$ $(C_4H_9COCHCO-t-C_4H_9)$, $Rh_2O_3$, $Rh_4(CO)_{12}$, $Rh_6(CO)_{16}$, $Rh(O_2CCH_3)_2$, Rh(2-ethylhexanoate), and combinations of two or more thereof.

The amount of transition metal in the catalyst can be any amount, so long as favorable results can be obtained with respect to catalyst activity and process economy. In general, the molar ratio of polymeric ligand to transition metal generally can be from about 1:1 to about 100:1, preferably from about 1:1 to about 20:1 (based on moles phosphorus per mole metal).

The reactant of the hydroformylation process is an unsaturated organic compound having at least one "C=C" bond in the molecule and preferably 2 to about 20 carbon atoms. Examples of suitable ethenically unsaturated organic compounds include, but are not limited to, linear terminal olefinic hydrocarbons, for example, ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; cyclic olefinic hydrocarbons, for example, cyclohexene, cyclopentene, branched terminal olefinic hydrocarbons, for example, isobutene and 2-methyl-1-butene; linear internal olefinic hydrocarbons, for example, cis- and trans-2-butene, cis- and trans-2-hexene, cis- and trans-2-octene, cis- and trans-3-octene; branched internal olefinic hydrocarbons, for example, 2,3-dimethyl-2-butene, 2-methyl-2-butene and 2-methyl-2-pentene; terminal olefinic hydrocarbons; internal olefinic hydrocarbon mixtures; for example, octenes, prepared by dimerization of butenes; cyclic olefins, for example, cyclohexene, cyclooctene; and combinations of two or more thereof.

Examples of suitable olefinic compounds also include those substituted with an unsaturated hydrocarbon group, including olefinic compounds containing an aromatic substituent such as styrene, alpha-methylstyrene and allylbenzene.

The unsaturated organic compound can also be substituted with one or more functional groups containing a heteroatom, such as oxygen, sulfur, nitrogen or phosphorus. Examples of these heteroatom-substituted ethenically unsaturated organic compounds include vinyl methyl ether, methyl oleate, oleyl alcohol, 3-pentenenitrile, 4-pentenenitrile, 3-pentenoic acid, 4-pentenoic acid, methyl 3-pentenoate, 7-octen-1-al, acrylonitrile, acrylic acid esters, methyl acrylate, methacrylic acid esters, methyl methacrylate, acrolein, allyl alcohol, 3-pentenal, 4-pentenal, and combinations of two or more thereof.

The hydroformylation process of the invention can be illustrated as follows:

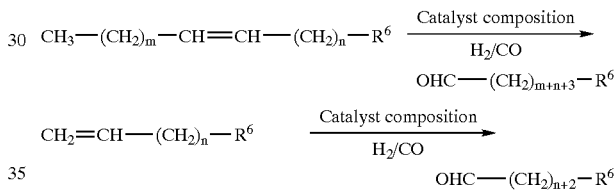

In the above equations, $R^6$ is H, —CN, —$CO_2R^7$, —C(O)$NR^7R^7$, —CHO, —$OR^7$, OH, or combinations of two or more thereof; y is an integer from 0 to 12; and x is an integer from 0 to 12. Each $R^7$ is independently selected from the group consisting of H, $C_1$ to $C_{20}$ branched or straight chain alkyl, $C_1$ to $C_{20}$ cycloalkyl, and $C_6$ to $C_{20}$ aryl.

Particularly preferred unsaturated organic compounds are 3-pentenenitrile, 3-pentenoic acid, 3-pentenal, allyl alcohol, and alkyl 3-pentenoate, such as methyl 3-pentenoate, and combinations of two or more thereof. The linear aldehyde compound prepared by the present process starting with one of these compounds can be used advantageously in the preparation of caprolactam, hexamethylenediamine, 6-aminocaproic acid, 6-aminocapronitrile or adipic acid, which are precursors for Nylon-6 and/or Nylon-6,6.

The hydroformylation process of the invention also can be carried out with a mixture that comprises two or more unsaturated organic compounds. For example, 3-pentenenitrile can be present in a mixture containing 4-pentenenitrile. Because the 4-isomer reacts in a similar fashion as the corresponding 3-isomer to the desired linear aldehyde, a mixture of isomers can be used directly in the present process.

The 3-pentenenitrile may be present in mixtures containing impurities that do not interfere with the hydroformylation reaction. An example of such an impurity is 2-pentenenitrile.

The hydroformylation process of the invention can be carried out by any means known to one skilled in the art, such as, for example, the one disclosed in U.S. Pat. No.

4,769,498 the disclosure of which is incorporated herein by reference. Generally, the process can be carried out under any condition sufficient to effect the production of a desired aldehyde. For example, the temperature can be from about 0° C. to 200° C., preferably from about 50 to 150° C., and more preferably from 85° C. to 110° C. The pressure may vary from normal pressure to 5 MPa, preferably from 0.1 to 2 MPa. The pressure is, as a rule, equal to the combined hydrogen and carbon monoxide partial pressures. Inert gases also may be present; the pressure may vary from normal pressure to 15 MPa when inert gases are present. The molar ratio of hydrogen to carbon monoxide is generally between 10:1 and 1:10, and preferably between 6:1 and 1:2. It is most preferred that a 1:1 ratio of carbon monoxide and hydrogen is used.

The amount of catalyst is selected so that favorable results can be obtained with respect to catalyst activity and process economy. In general, the concentration of transition metal in the reaction medium, which comprises an unsaturated organic compound, a catalyst composition, and solvent (if present), can be between 10 and 10,000 ppm and more preferably between 50 and 1,000 ppm, calculated as free metal.

The molar ratio of the present polymeric ligand to transition metal is selected so that favorable results can be obtained with respect to catalyst activity and desired aldehyde selectivity. This ratio generally is from about 1 to 100 and preferably from 1 to 20 (moles phosphorus per mole metal).

The solvent may be the mixture of reactants of the hydroformylation reaction itself, such as the starting unsaturated compound, the aldehyde product and/or by-products. Other suitable solvents include saturated hydrocarbons (for example, kerosene, mineral oil, or cyclohexane), ethers (for example, diphenyl ether or tetrahydrofuran), ketones (for example, acetone, cyclohexanone), nitriles (for example, acetonitrile, adiponitrile or benzonitrile), aromatics (for example, toluene, benzene, or xylene), esters (for example, methyl valerate, caprolactone), Texanol® (Union Carbide), dimethylformamide, or combinations of two or more thereof.

The hydroformylation process can be run in solution or in the gas phase. When the hydroformylation is carried out in the vapor phase, the preferred temperature range is from about 50° C. to about 180° C., most preferably from about 90° C. to 110° C. The temperature must be chosen so as to maintain all of the reactants and products in the vapor phase, but low enough to prevent deterioration of the catalyst. The particular preferred temperature depends to some extent on the catalyst being used, the olefinic compound being used, and the desired reaction rate. The operating pressure is not particularly critical and can be from about 0.101 to 1.01 MPa. The pressure and temperature combination must be chosen so as to maintain reactants and products in the vapor phase. A given catalyst is loaded into a reactor, such as a tubular reactor, taking care to avoid exposure of air-sensitive catalysts to oxygen from the air. A gaseous mixture of the desired olefinic compound, carbon monoxide and hydrogen, along with any desired diluent, such as nitrogen, helium or argon, is then passed through the reactor while contacting the catalyst. The reaction products are generally liquid at room temperature and are conveniently recovered by cooling. The reactor effluent can be directly connected to a sampling valve and can be analyzed by gas chromatography. Aldehydic products, such as linear and branched butyraldehydes obtained from hydroformylation of propylene, can be quantitatively separated and analyzed using a 30 M DB-Wax® capillary GC column.

EXAMPLES

The following non-limiting, representative examples illustrate the processes for the preparation of the ligands and catalysts of this invention. Unless otherwise specificed, all chemicals and reagents were used as received from Aldrich Chemical Co., Milwaukee, Wis. Legend:

1-Pr means isopropyl alcohol (o-iPrC$_6$H$_4$O)$_2$ means isopropyl phenyl

SL means supported ligand

SC means supported catalyst and the number corresponds to the SL number.

Example 1

Grafting 3,3'-Diisopropyl-6,6'-Dimethyl-2,2'-Biphenol onto Merrifield Resin

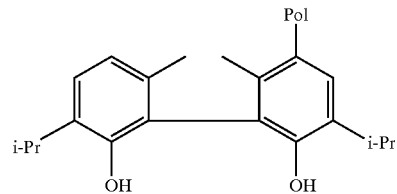

A mixture of 3,3'-diisopropyl-6,6'-dimethyl-2,2'-biphenol (1.0 g), Merrifield resin (1.0 g, 1.9 mmol Cl), ZnCl$_2$ (0.2 g) and 1,2-dichloroethane (6 mL) was stirred at over night and 70° C. for 4 days. The solid was filtered, washed with hexanes (2×10 mL) and methanol (3×10 mL), dried on full vacuum to give a solid (1.28 g).

Example 1A

Preparation Polymer-Supported Ligand (SL 1) from the Reaction of 3,3'-diisopropyl-6,6'-dimethyl-2,2'-biphenol Grafted Merrifield Resin and Di(2-isopropylphenyl) Phosphorochloridite

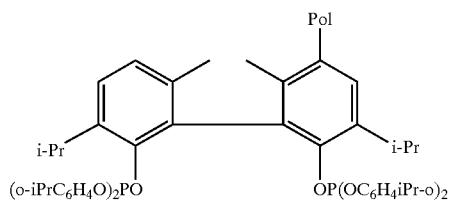

A mixture of the polymer (0.5 g) from example 1 and di(2-isopropylphenyl) phosphorochloridite (1.0 g) was stirred in about 20 mL of tetrahydrofuran (THF) for 30 min. Tri-n-butylamine (1.0 g) was added to the mixture. The resulting mixture was stirred at room temperature for 4 days. The solid was collected by filtration and washed with acetonitrile (2×20 mL), and vacuum dried to give 0.7 g of the ligand.

Elemental analysis: P % 2.4.

17

Example 2

Grafting 3,3'6,6'-Tetramethyl-5,5'-diisopropyl-2,2'-biphenol onto Merrifield Resin

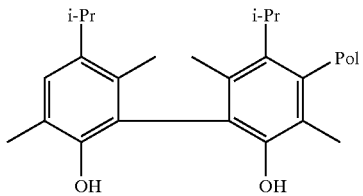

A mixture of 3,3'6,6'-tetramethyl-5,5'-diisopropyl-2,2'-biphenol (0.7 g), Merrifield resin (0.5 g, 0.95 mmol Cl), AlCl$_3$ (50 mg) and 1,2-dichloroethane (6.5 g) was stirred at room temperature for 3 days and 70° C. for 2 hours. The solid was filtered, washed with hexanes (2×30 mL) and methanol (3×30 mL), dried on full vacuum to give a solid (0.64 g).

Example 2A

Preparation Polymer-Supported Ligand (SL 2) from the Reaction 3,3'6,6'-tetramethyl-5,5'-diisopropyl-2,2'-biphenol Grafted Merrifield Resin and Di2-methylphenyl) Phosphorochloridite

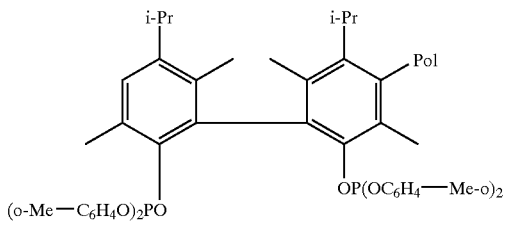

A mixture of the polymer (0.6 g) from Example 2 and di(2-methylphenyl) phosphorochloridite (1.1 g) was stirred in about 30 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.8 g of the ligand. Elemental analysis: P % 4.7.

Example 3

Grafting 3,3'-Diisopropyl-5,5'-Dimethyl-2,2'-biphenol onto Merrifield Resin

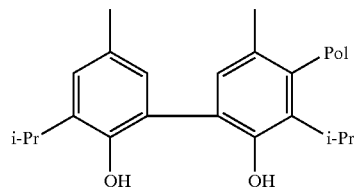

A mixture of 3,3'-diisopropyl-5,5'-dimethyl-2,2'-biphenol (1.0 g), Merrifield resin (1.0 g, 1.9 mmol Cl), AlCl$_3$ (50 mg) and 1,2-dichloroethane (10 mL) was stirred at room temperature for 3 days and 70° C. for 1 day. The solid was filtered, washed with hexanes (2×20 mL) and methanol (2×20 mL), dried on full vacuum to give a solid (1.4 g).

18

Example 3A

Preparation Polymer-Supported Ligand (SL 3) from the Reaction of 3,3'-diisopropyl-5,5'-dimethyl-2,2'-biphenol Grafted Merrifield Resin and Di(2-methylphenyl) Phosphorochloridite

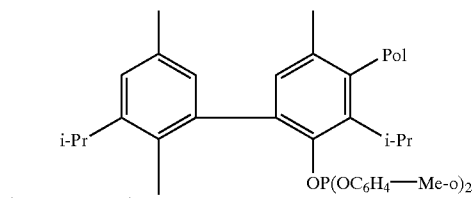

A mixture of the polymer (0.5 g, same composition as from Example 3, but different batch) and di(2-methylphenyl) phosphorochloridite (1.0 g) was stirred in about 30 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.72 g of the ligand. Elemental analysis: P % 5.2.

Example 4

Grafting 3,3',4,4',6,6'-hexamethyl-2,2'-biphenol onto Merrifield Resin

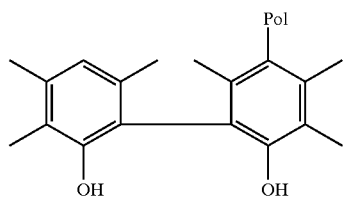

A mixture of 3,3',4,4',6,6'-hexamethyl-2,2'-biphenol (1.0 g), Merrifield resin (1.0 g, 1.9 mmol Cl), AlCl$_3$ (50 mg) and 1,2-dichloroethane (10 mL) was stirred at room temperature for 3 days and 70° C. for 1 day. The solid was filtered, washed with hexanes (2×20 mL) and methanol (2×20 mL), dried on full vacuum to give a solid (1.15 g).

Example 4A

Preparation Polymer-Supported Ligand (SL 4) from the Reaction of 3,3',4,4',6,6'-hexamethyl-2,2'-biphenol Grafted Merrifield Resin and Di(2-isopropylphenyl) Phosphorocloridite

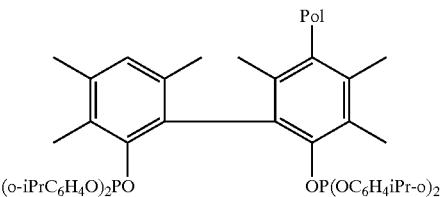

A mixture of the polymer (0.50 g, from Example 4) and di(2-isopropylphenyl) phosphorochloridite (1.0 g) was stirred in 20 mL of tetrahydrofuran (THF) for 30 min.

Tri-n-butylamine (1.0 g) was added to the mixture. The resulting mixture was stirred at room temperature for 4 days. The solid was collected by filtration and washed with acetonitrile (2×20 mL), and vacuum dried to give 0.6 g of the ligand. Elemental analysis: P % 3.47.

Example 5

Grafting 3,3'-diisopropyl-5,5'-di-t-butyl-6,6'-dimethyl-2,2'-biphenol onto Merrifield Resin

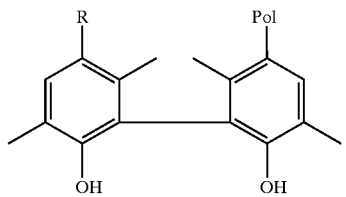

R: H, t-Bu

A mixture of 3,3'-diisopropyl-5,5'-di-t-butyl-6,6'-dimethyl-2,2'-biphenol (1.1 g), Merrifield resin (1.1 g, 2.1 mmol Cl), AlCl$_3$ (50 mg) and 1,2-dichloroethane (10 mL) was stirred at room temperature for 3 days and 70° C. for 1 day. The solid was filtered, washed with hexanes (2×20 mL) and methanol (2×20 mL), dried on full vacuum to give a solid (1.2 g).

Example 5A

Preparation Polymer-Supported Ligand (SL 5) from the Reaction of 3,3'-diisopropyl-5,5'-di-t-butyl-6,6'-dimethyl-2,2'-biphenol Grafted Merrifield Resin and Di(2-isopropylphenyl) Phosphorocloridite

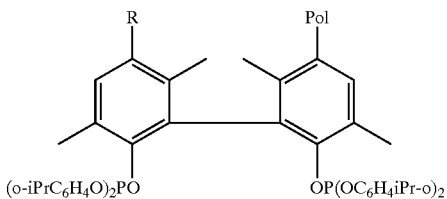

R: H, t-Bu

A mixture of the polymer (1.0 g, from Example 5) and di(2-isopropylphenyl) phosphorochloridite (1.0 g) was stirred in about 15 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 1.8 g of the ligand. Elemental analysis: P % 1.34.

Example 6

Grafting 3,3',5,5'-tetraisopropyl-6,6'-dimethyl-2,2'-biphenol onto Merrifield Resin

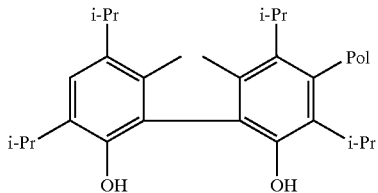

A mixture of 3,3',5,5'-tetraisopropyl-6,6'-dimethyl-2,2'-biphenol (1.1 g), Merrifield resin (1.1 g, 2.1 mmol Cl), AlCl$_3$ (50 mg) and 1,2-dichloroethane (10 mL) was stirred at room temperature for 3 days and 70° C. for 1 day. The solid was filtered, washed with hexanes (2×20 mL) and methanol (2×20 mL), dried on full vacuum to give a solid (0.8 g).

Example 6A

Preparation Polymer-Supported Ligand (SL 6) from the Reaction of 3,3',5,5'-tetraisopropyl-6,6'-dimethyl-2,2'-biphenol Grafted Merrifield Resin and Di(2-iopropylphenyl) Phosphorocloridite

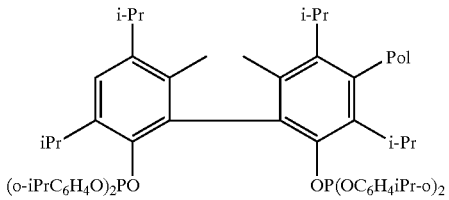

A mixture of the polymer (0.5 g, from Example 6) and di(2-isopropylphenyl) phosphorochloridite (1.0 g) was stirred in about 15 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 1.22 g of the ligand. Elemental analysis: P % 1.1.

Example 7

Grafting 2,2'-binaphthol onto Merrifield Resin

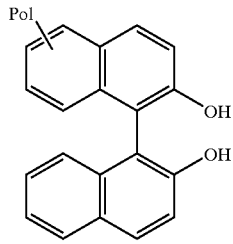

A mixture of 2,2'-binaphthol (1.5 g), Merrifield resin (0.5 g, 2.21 mmol Cl), ZnCl$_2$ (0.2 g) and 1,2-dichloroethane (5 mL) was stirred at 70° C. for 3 days. The solid was filtered, washed with hexanes (2×20 mL) and methanol (2×20 mL), dried on full vacuum to give a solid (1.0 g).

Example 7A

Preparation of Polymer-Supported Ligand (SL 7) from the Reaction 2,2'-binaphthol Grafted Merrifield Resin and Di(2-methylphenyl) Phosphorocloridite

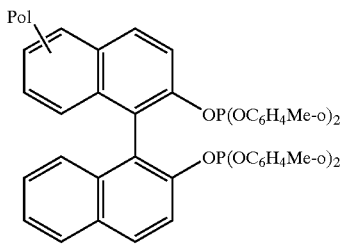

A mixture of the polymer (0.5 g, from example 7) and di(2-methylphenyl) phosphorochloridite (1.8 g) was stirred in about 30 mL of tetrahydrofuran (THF) for 30 min. Tri-n-butylamine (1.0 g) was added to the mixture. The resulting mixture was stirred at room temperature for 5 days. The solid was collected by filtration and washed with acetonitrile (2×20 mL), and vacuum dried to give 0.49 g of the ligand. Elemental analysis: P % 5.5.

Example 8

Grafting 5,5',6,6',7,7',8,8'-octahydro-3-isopropyl-2,2'-binaphthol onto Merrifield Resin

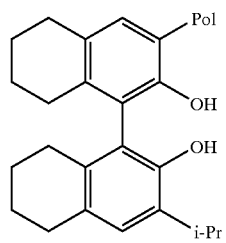

A mixture of 5,5',6,6',7,7',8,8'-octahydro-3-isopropyl-2,2'-binaphthol (1.5 g), Merrifield resin (0.5 g, 2.2 mmol Cl), ZnCl$_2$ (0.1 g) and 1,2-dichloroethane (5 mL) was stirred at 70° C. for 3 day. The solid was filtered, washed with hexanes (2×50 mL) and methanol (2×50 mL), dried on full vacuum to give a solid (1.26 g).

Example 8A

Preparation of Polymer-Supported Ligand (SL 8) from the Reaction of 5,5',6,6',7,7',8,8'-octahydro-3-isopropyl-2,2'-binaphthol Grafted Merrifield Resin and Di(2-methylphenyl) Phosphorocloridite

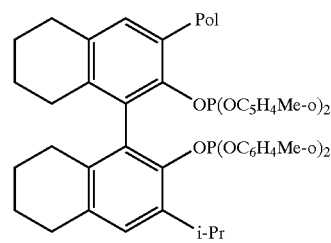

A mixture of the polymer (0.5 g, from example 8) and di(2-methylphenyl) phosphorochloridite (1.8 g) was stirred in about 40 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.72 g of the ligand. Elemental analysis: P % 5.6.

Example 8B

Preparation Polymer-Supported Ligand (SL 9) from the Reaction of 5,5',6,6',7,7',8,8'-octahydro-3-isopropyl-2,2'-binaphthol Grafted Merrifield Resin and Di(2-isopropylphenyl) Phosphorocloridite

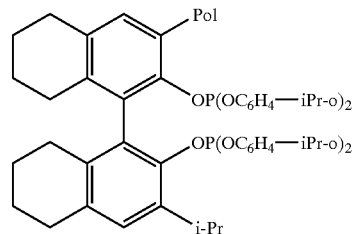

A mixture of the polymer (0.35 g, from Example 8) and di(2-isopropylphenyl) phosphorochloridite (1.0 g) was stirred in about 20 mL of tetrahydrofuran (THF) for 30 min. Tri-n-butylamine (1.0 g) was added to the mixture. The resulting mixture was stirred at room temperature for 4 days. The solid was collected by filtration and washed with acetonitrile (2×20 mL), and vacuum dried to give 0.5 g of the ligand. Elemental analysis: P % 3.1.

Example 9

Grafting 3,3',5,5',6,6'-hexamethyl-2,2'-biphenol onto Merrifield Resin

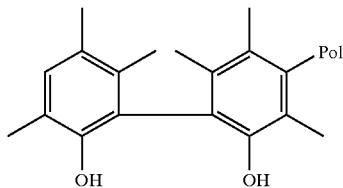

A mixture of 3,3',5,5'6,6'-hexamethyl-2,2'-biphenol (0.89 g), Merrifield resin (1.0 g, 1.9 mmol Cl), AlCl$_3$ (0.1 g) and 1,2-dichloroethane (20 mL) was stirred at room temperature for 2 days and 70° C. for 8 hours. The solid was filtered, washed with hexanes (2×20 mL) and methanol (3×20 mL), dried on full vacuum to give a solid (1.2 g).

Example 9A

Preparation Polymer-Supported Ligand (SL 10) from the Reaction of 3,3',5,5'6,6'-hexamethyl-2,2'-biphenol Grafted Merrifield Resin and Di(2-methylphenyl) Phosphorocloridite

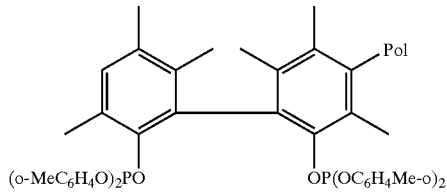

A mixture of the polymer (0.5 g, from Example 9) and di(2-methylphenyl) phosphorochloridite (1.5 g) was stirred in 50 mL of tetrahydrofuran (THF). Tri-n-butylamine (1.0 g) was added to the mixture at 0° C. The resulting mixture was stirred at room temperature for 3 days. The solid was collected by filtration and washed with acetonitrile (2×20 mL), and vacuum dried to give 0.59 g of the ligand. Elemental analysis: P % 3.1.

Example 10

Grafting 3,3'-diisopropyl-5,5',6,6'-tetramethyl-2,2'-biphenol onto Merrifield Resin

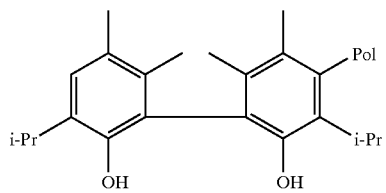

A mixture of 3,3'-diisopropyl-5,5',6,6'-tetramethyl-2,2'-biphenol (1.0 g), Merrifield resin (1.0 g, 1.9 mmol Cl/g), AlCl$_3$ (50 mg) and 1,2-dichloroethane (10 mL) was stirred at room temperature for 3 days and 70° C. for 1 day. The solid was filtered, washed with hexanes (2×20 mL) and methanol (2×20 mL), dried on full vacuum to give a solid (0.34 g).

Example 10A

Preparation of Polymer-Supported Ligand (SL 11) from the Reaction of 3,3'-diisopropyl-5,5',6,6'-tetramethyl-2,2'-biphenol Grafted Merrifield Resin and Di(2-methylphenyl) Phosphorocloridite

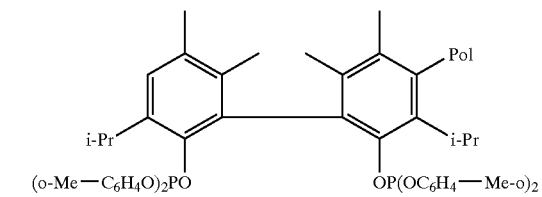

A mixture of the polymer (0.4 g, same composition as from Example 10, but different batch) and di(2-methylphenyl) phosphorochloridite (1.0 g) was stirred in about 30 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.5 g of the ligand. Elemental analysis: P % 3.3.

Example 11

Grafting 3,3',5,5'-tetramethyl-2,2'-biphenol onto Merrifield Resin

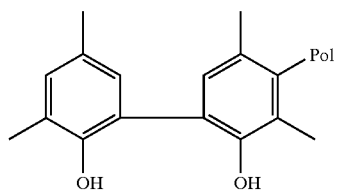

A mixture of 3,3',5,5'-tetramethyl-2,2'-biphenol (1.0 g), Merrifield resin (1.0 g, 1.9 mmol Cl), AlCl$_3$ (50 mg) and 1,2-dichloroethane (10 g) was stirred at room temperature for 3 days and 70° C. for 1 day. The solid was filtered, washed with hexanes (2×20 mL) and methanol (2×30 mL), dried on full vacuum to give a solid (0.88 g).

Example 11A

Preparation of Polymer-Supported Ligand (SL 12) from the Reaction of 3,3',5,5'-tetramethyl-2,2'-biphenol Grafted Merrifield Resin and Di(2-methylphenyl) Phosphorocloridite

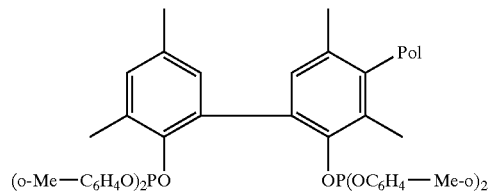

A mixture of the polymer (0.5 g, same composition as from example 11, but different batch) and di(2-methylphenyl) phosphorochloridite (1.0 g) was stirred in about 30 mL of tetrahydrofuran (THF) for 30 min. Tri-n- butylamine (1.0 g) was added to the mixture. The resulting mixture was stirred at room temperature for 3 days. The solid was collected by filtration and washed with acetonitrile (2×20 mL), and vacuum dried to give 0.6 g of the ligand. Elemental analysis: P % 5.0.

Example 11B

Preparation Polymer-Supported Ligand (SL 13) from the Reaction of 3,3',5,5'-tetramethyl-2,2'-biphenol Grafted Merrifield Resin and Di(2-isopropylphenyl) Phosphorocloridite

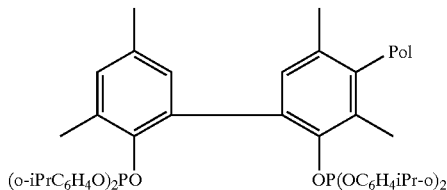

(o-iPrC$_6$H$_4$O)$_2$PO      OP(OC$_6$H$_4$iPr-o)$_2$

A mixture of the polymer (0.5 g, from Example 11) and di(2-isopropylphenyl) phosphorochloridite (1.0 g) was stirred in about 20 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.53 g of the ligand. Elemental analysis: P % 2.6.

Example 12

Grafting 3,3',4,4',6.6'-hexamethyl-2,2'-biphenol onto Polyvinylbenzyl Chloride

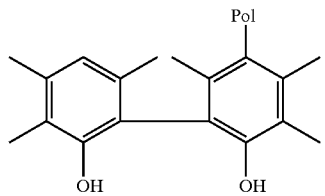

In a vial was added 0.595 g of poly(vinylbenzylchloride) (from Aldrich, catalog number: 18253-2; 60/40 mix of 3 and 4 isomers; average Mn 55,000; Mw 100,000) and 1.000 g of 3,3',4,4',6,6'-hexamethyl-2,2'-biphenol, 25 mg of zinc chloride and 10 mL of methylene chloride. The vial was capped and heated at 50° C. for 45 minutes. The resultant gel was broken up with a spatula and 5 mL more of methylene chloride was added. After heating overnight, the solvent was removed under vacuum and the residue washed with acetone and water. The solid was filtered, washed with water and vacuum dried to give 1.257 g of a tan solid. Elemental analysis found: C: 82.93%; H: 7.61% and Cl: 1.77%.

Example 12A

Preparation of Polymer-Supported Ligand (SL 14) from the Reaction of 3,3',4,4',6.6'-hexamethyl-2,2'-biphenol Grafted Polyvinylbenzyl Chloride and Di (2-methylphenyl) Phosphorocloridite

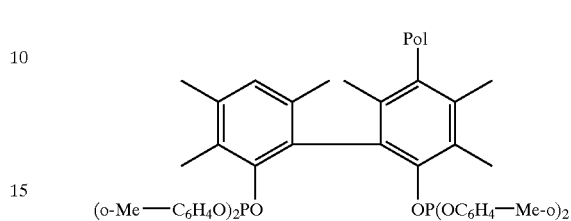

(o-Me—C$_6$H$_4$O)$_2$PO      OP(OC$_6$H$_4$—Me-o)$_2$

A flask was charged with 0.7775 of the tan solid from example 12, 1.123 g of the phosphorochloridite of o-cresol and 15 mL of tetrahydrofuran (THF). Tri-n-butylamine (1.2 g) was added dropwise and the mixture stirred at room temperature for two days and then heated at 40C for two days. Around 25 mL of acetonitrile was added and the mixture concentrated by rotary evaporation. More acetonitrile (about 10 mL) was added. The off-white solid was filtered and washed with acetonitrile and vacuum dried to give 0.944 g of material. Elemental analysis: C: 77.02%; H: 6.61%, P: 4.96%, Cl: 1.69%.

Example 13

Treatment of Polystyrene (Crosslinked with 2% of Divinylbenzene) with DDQ

A mixture of the polystyrene (2.0 g) and DDQ (0.76 g) was stirred in about 30 mL of toluene at 85° C. for 4 hours. The resin was filtered, washed with toluene, acetonitrile, acetone, ethyl acetate (2×20 mL for each of the solvent), and vacuum dried to give 1.8 g of brown solid.

Example 13A

Grafting 3,3'-diisopropyl-6,6'-dimethyl-2,2'-biphenol onto the Polymer from Example 13

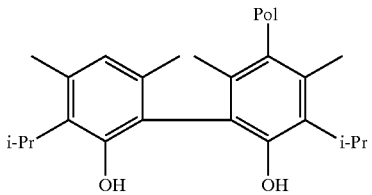

A mixture of a solid from example 13 (1.7 g), 3,3'-diisopropyl-6,6'-dimethyl-2,2'-biphenol(1.0 g), phosphotungstic acid (0.1 g) and chlorobenzene (5 mL) was stirred at 65° C. for 2 days. After adding hexanes (20 mL), the resin was filtered, washed with sodium bicarbonate (aq. sat., 2×20 mL), water (3×20 mL), MeOH (2×20 mL) and acetone (2×20 mL), and vacuum dried at 60° C. for 10 hours to give 0.9 g of solid.

Example 13B

Preparation Polymer-Supported Ligand (SL 15) from the Reaction of Resin from Example 16A and Di(2-methylphenyl) Phosphorocloridite

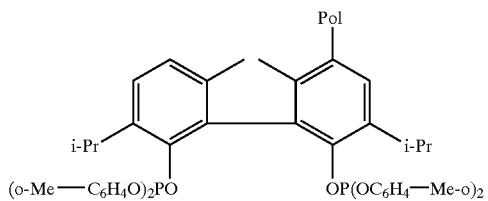

A mixture of the polymer (0.5 g, from Example 13A) and di(2-methylphenyl) phosphorochloridite (1.5 g) was stirred in about 30 mL of tetrahydrofuran (THF) for 30 min. Tri-n-butylamine (1.0 g) was added to the mixture. The resulting mixture was stirred at room temperature for 3 days. The solid was collected by filtration and washed with acetonitrile (2×20 mL), and vacuum dried to give 0.63 g of the ligand. Elemental analysis: P % 1.6.

Example 14

Grafting 2,2'-binaphthol onto Polyvinylbenzyl Chloride

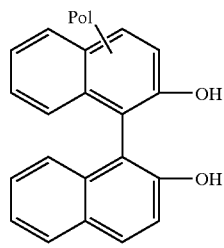

In a vial was added 0.534 g of poly(vinylbenzylchloride) (from Aldrich, catalog number: 18253-2; 60/40 mix of 3 and 4 isomers; average Mn 55,000; Mw 100,000) and 1.001 g of binaphthol, 30 mg of zinc chloride and 7 mL of methylene chloride. The vial was capped and heated at 50° C. for 3 hours. The resultant gel was broken up with a spatula and 3 mL more of methylene chloride was added. After heating at 70° C. for two days, the solid was filtered to give 0.925 g of pink solid.

Example 14A

Preparation of Polymer-Supported Ligand (SL 16) from the Reaction of 2,2'-binaphthol Grafted Polyvinylbenzyl Chloride and Di(2-methylphenyl) Phosphorocloridite

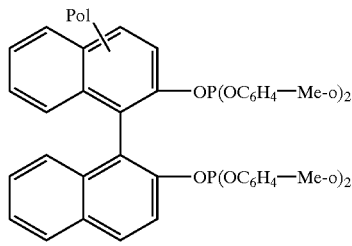

A flask was charged with 0.905 of the pink solid from Example 14, 1.123 g of the phosphorochloridite of o-cresol and 15 mL of tetrahydrofuran (THF). Tri-n-butylamine (1.2 g) was added dropwise and the mixture stirred at room temperature for three days and then heated at 40° C. for two days. Around 10 mL of acetonitrile was added and the mixture concentrated by rotary evaporation. More acetonitrile (about 30 mL) was added. The pale yellow solid was filtered and washed with acetonitrile and vacuum dried to give 0.961 g of material. Elemental analysis: C: 76.62%; H: 5.65%, P: 4.56%, Cl: 0%.

Example 15

Hydrocyanation and Isomerization Processes—Results with Polymer-Supported Catalyst from Example 4A (SL 4)

Preparation of catalyst: A catalyst suspension was prepared by adding 0.0039 g of Ni(COD)$_2$ (0.014 mmol) in 0.320 mL toluene to 0.038 g of SL 4 (0.021 mmol) in 0.200 mL toluene in a vial.

Hydrocyanation of butadiene: The above catalyst suspension (0.014 mmol Ni) was cooled to −20° C. and 120 µl of a solution of HCN in valeronitrile (0.830 mmol HCN) and 280 µl of a solution of butadiene (BD) in toluene (0.925 mmol BD) were added to the catalyst suspension. The vials was sealed and placed in a hot-block reactor set at 80° C. Sample was removed after 3 hours and cooled. The reaction mixture was then diluted in ethyl ether and analyzed by GC against valeronitrile as an internal standard. Analysis showed that 90% of the starting HCN had been converted to useful pentenenitriles (the 3-pentenenitrile to 2-methyl-3-butenenitrile ratio was 1.6).

Isomerization of 2-methyl-3-butene nitrile (2M3BN): A catalyst suspension (0.014 mmol Ni), prepared according the above procedure, was cooled to −20° C. and 130 µl of a cold solution containing 2M3BN (0.930 mmol) and valeronitrile was added to the vial. The vial was sealed and placed in a hot block reactor set at 125° C. Sample was removed after 3.0 hrs, cooled and diluted in ethyl ether. The product distribution was analyzed by GC using valeronitrile as an internal standard. The 3PN/2M3BN ratio was 18.8 after 3 hours.

Hydrocyanation of 3-Pentenenitrile (3-PN): A catalyst suspension (0.014 mmol Ni), prepared according the above procedure was placed in a vial. The vial was cooled to −20° C. and 125 µL of a solution made from HCN (1.622 g, 60 mmol), t-3PN (12.168 g, 147 mmol), and 2-ethoxyethyl ether (1.21 g, 7.45 mmol) was added. Then 13 µL of a solution made from ZnCl$_2$ (0.208 g) and 3PN (2.772 g) were added to the vial. The vial was sealed and set aside for 24 hours at room temperature. The reaction mixture was diluted with ethyl ether and the product distribution analyzed by GC using 2-ethoxyethyl ether as an internal standard. Analysis showed that 25% of the starting pentenenitriles had been converted to dinitrile product (68% yield based on HCN.) The selectivity to the linear ADN isomer was 96.3%.

Example 16

General Scouting Procedure (Semibatch) Hydrocyanation Results with Polymer-Supported Catalyst from Example 12A (SL 14)

Preparation of Catalyst:

The nickel catalyst was prepared by treating 400 mg of the off-white solid from example 12A with 63 mg of Ni(COD)2 in 4 mL of THF. After stirring for 2–3 hours, the solvent was removed under vacuum.

Hydrocyanation of 3-Pentenenitrile (3PN):

A three necked flask was charged with 0.284 g of the above nickel catalyst, 19 mg of zinc chloride and 5 mL of 3-pentenenitrile. The hydrocyanation reaction was done at a nitrogen flow rate of 12 cc/min with the oil bath at 50° C. for 180 minutes and then 70° C. for 120 minutes. GC analysis indicated 87% of the pentenenitriles have converted to dinitriles with an adiponitrile distribution of 93%.

TABLE 1

Isomerization of 2M3BN to 3PN

| Example | Supported Ligand/ Supported Catalyst | 3PN/2M3 Ratio |
|---|---|---|
| 15-1 | SL/SC 1 | 4.9 |
| 15-2 | SL/SC 2 | 0.2 |
| 15-3 | SL/SC 3 | 18.3 |
| 15-4 | SL/SC 4 | 1.3 |
| 15-5 | SL/SC 5 | 18.5 |
| 15-6 | SL/SC 6 | 11.5 |
| 15-8 | SL/SC 8 | 0.6 |
| 15-9 | SL/SC 9 | 17.5 |
| 15-10 | SL/SC 10 | 0.02 |
| 15-11 | SL/SC 11 | 0.7 |
| 15-12 | SL/SC 12 | 6.9 |
| 15-13 | SL/SC 13 | 1.8 |
| 15-14 | SL/SC 14 | 8.54 |
| 15-15 | SL/SC 15 | 0.07 |
| 15-16 | SL/SC 16 | 0.9 |

The results were obtained by the procedure described in the Example 15.

TABLE 2

Hydroformylation of 3PN

| Example | Suppoted Ligand/ Supported Catalyst | 3PN Conversion | Selectivity to 5-formylvalerontrile | Linearity of aldehydes produced | Reduction Product (%) |
|---|---|---|---|---|---|
| 16-1 | SL/SC 2 | 76 | 83 | 95 | 12 |
| 16-2 | SL/SC 5 | 52 | 45 | 54 | 14 |
| 16-3 | SL/SC 6 | 29 | 40 | 20 | 20 |
| 16-4 | SL/SC 8 | 40 | 46 | 56 | 37 |
| 16-5 | SL/SC 9 | 28 | 4 | 8 | 37 |
| 16-6 | SL/SC 13 | 38 | 38 | 48 | 19 |
| 17-7 | SL/SC 15 | 10 | 27 | 52 | 25 |

Example 17

General Scouting Procedure Hydroformylation of 3-pentenenitrile with Polymeric Phosphite from Example 2A:

In a drybox, a solution containing 3-pentenenitrile (5.0 g), Rh(CO)2 (acac) (2.5 mg), and 1,2-dichlorobenzene (internal standard, 0.27 M) was prepared. This solution was added to a glass-lined pressure vessel containing approximately two equivalents of the polymeric phosphite described in Example 2A per equivalent of rhodium. The reactor was sealed, pressurized to 65 psig with a 1:1 molar ratio of CO/H2 and heated to 95° C. for 3 hours. The reactor was cooled and depressurized and a sample of the reaction mixture was analyzed by gas chromatography on an HP 5890A Chromatograph with a DB5 fused silica capillary column (30 meters, 0.32 mm I.D.) purchased from J. B. Scientific. GC analysis: 76.1% conversion; selectivity to 5-formylvaleronitrile: 82.7% on a mole basis; linearity of aldehydes produced: 95.3%.

The results in Table 4 were obtained by the procedure described in the Example 16. The reduction product percent shown in the table above indicates the amount of hydrogenated products were obtained, based on converted 3PN.

What is claimed is:

1. A polymer-supported diol of the formula:

(1)

wherein Pol and Q are connected via a carbon-carbon bond; Q is an organic ring structure; and Pol is an insoluble polymer support;

comprising a diol grafted onto a polymer selected from the group consisting of a benzyl halide-containing polymer or a olefin-containing polymer; wherein the benzyl halide-containing polymer is attached to an aromatic carbon of the diol through a benzylic carbon or the olefin-containing polymer is attached to an aromatic carbon of the diol through an olefinic carbon; wherein said diol is selected from the group consisting of (a) biphenol, C,

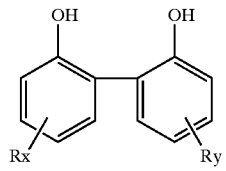

C wherein each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether; wherein neighboring $R^1$ groups are optionally connected to form a ring structure; wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl; and wherein x and y are each independently 0–3, and x and y are each independently 0–4 if at least one of $R_x$ or $R_y$ contains an aromatic ring; and (b) binaphthol, D,

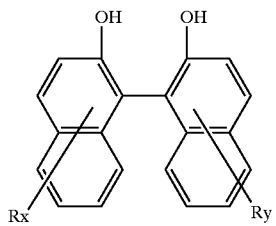

D wherein each R is independently selected from the group consisting of H, $C_1$ to $C_{20}$ branched or straight chain alkyl and benzyl, $C_1$ to $C_{20}$ cycloalkyl, $C_6$ to $C_{20}$ aryl, $OR^1$, $CO_2R^1$, and cyclic ether; wherein each $R^1$ is independently selected from the group consisting of $C_1$ to $C_{20}$ branched or straight chain alkyl, $C_1$ to $C_{20}$ cycloalkyl, and $C_6$ to $C_{20}$ aryl; wherein x and y are each independently 0–5, and x and y are each independently 0–6 if at least one of $R_x$ or $R_y$ contains an aromatic ring, and combinations thereof.

2. A polymer-supported bis(phosphorous) ligand (2) having the formula,

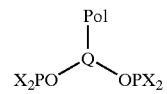

(2)

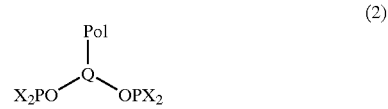

wherein Pol and Q are connected via a carbon-carbon bond; Q is an organic ring structure; Pol is an insoluble polymer support; and X is selected from the group of alkoxide, aryloxide, alkyl or aryl;

comprising the reaction product of the polymer supported diol of claim 1 with a phosphorous halide of the formula $PY_nX_{3-n}$, wherein Y is a halide; X is selected from the group consisting of alkoxide, aryloxide, alkyl and aryl; and n=3, 2, or 1; and wherein, when X is an alkoxide, aryloxide, alkyl or aryl, X may contain from 1 to 50 carbon atoms, heteroatoms, or functional groups selected from the group consisting of ethers, alcohols, esters, and amides.

3. The polymer-supported diol of claim 1 wherein the benzyl halide-containing polymer is attached to an aromatic carbon of the diol through a benzylic carbon or the olefin-containing polymer is attached to an aromatic carbon of the dial through an olefinic carbon.

4. A polymer-supported bis(phosphorous) ligand (2) having the formula, (2)

wherein Pol and Q are connected via a carbon-carbon bond; Q is an organio ring structure; Pol is an insoluble polymer support; and X is selected from the group of alkoxide; aryloxide, alkyl or aryl;

comprising the reaction product of the polymer supported dial of claim 3 with a phosphorous halide of the formula $PY_nX_{3-n}$, wherein Y is a halide; X is selected from the group consisting of alkoxide, aryloxide, alkyl and aryl; and n=3, 2, or 1; and wherein, when X is an alkoxide, aryloxide, alkyl or aryl, X may contain from 1 to 50 carbon atoms, heteroatoms, or functional groups selected from the group consisting of ethers, alcohols, esters, and amides.

* * * * *